United States Patent
Yamamoto et al.

(10) Patent No.: US 9,758,819 B2
(45) Date of Patent: Sep. 12, 2017

(54) PCR ASSAY FOR ANIMAL ORIGIN OF HEPARIN

(71) Applicants: Ralph Yamamoto, Naperville, IL (US); Enrico Giuseppe Bellomo, Schaumburg, IL (US)

(72) Inventors: Ralph Yamamoto, Naperville, IL (US); Enrico Giuseppe Bellomo, Schaumburg, IL (US)

(73) Assignee: NantPharma, LLC, Los Angeles, CA (US)

( * ) Notice: Subject to any disclaimer, the term of this patent is extended or adjusted under 35 U.S.C. 154(b) by 104 days.

(21) Appl. No.: 14/434,667

(22) PCT Filed: Oct. 12, 2012

(86) PCT No.: PCT/US2012/059918
§ 371 (c)(1),
(2) Date: Apr. 9, 2015

(87) PCT Pub. No.: WO2014/058434
PCT Pub. Date: Apr. 17, 2014

(65) Prior Publication Data
US 2015/0267252 A1    Sep. 24, 2015

(51) Int. Cl.
*C12Q 1/68* (2006.01)

(52) U.S. Cl.
CPC ......... *C12Q 1/6858* (2013.01); *C12Q 1/6876* (2013.01)

(58) Field of Classification Search
None
See application file for complete search history.

(56) References Cited

U.S. PATENT DOCUMENTS

| 6,197,553 B1 | 3/2001 | Lee et al. |
| 2005/0112592 A1 | 5/2005 | Sinha et al. |
| 2011/0262909 A1 | 10/2011 | Cargill et al. |

FOREIGN PATENT DOCUMENTS

| EP | 0 386 053 B1 | 1/1994 | |
| IT | WO 8904328 A1 * | 5/1989 | ......... C08B 37/0075 |

OTHER PUBLICATIONS

Huang (Species-specific identification of ruminant components contaminating industrial crude porcine heparin using real-time fluorescent qualitative and quantitative PCR, Anal Bioanal Chem. Feb. 2012;402(4):1625-34. doi: 10.1007/s00216-011-5590-2. Epub Dec. 7, 2011).*
Huang et al., Species-specific identification by inhibitor-controlled PCR of ruminant components contaminating industrial crude porcine heparin, Mol Cell Probes. Jun.-Aug. 2006;20(3-4):250-8. Epub Mar. 23, 2006.*
Budelier et al., Purification of DNA by anion-exchange chromatography, Curr Protoc Mol Biol. May 2001;Chapter 2:Unit2.1B.*
Concannon et al., *Anal. Bioanal. Chem.*, 399, 757-762 (2011).
Huang et al., *Anal. Bioanal. Chem.*, 402, 1625-1634 (2012).
Mendoza-Romero et al., *J. Food Protection*, 67(3), 550-554 (2004).
Qiagen Anion-Exchange Resin, http://web.archive.org/web/20051016180929/http://www1.qiagen.com/Plasmid/AnionExchangeResin.aspx (Oct. 16, 2005).
Walker et al., *Analytical Biochemistry*, 316, 259-269 (2003).
Zhang et al., *J. Virol. Methods*, 167(2), 158-164 (Aug. 2010).

* cited by examiner

*Primary Examiner* — Aaron Priest
(74) *Attorney, Agent, or Firm* — Leydig, Voit & Mayer, Ltd.

(57) ABSTRACT

The invention provides methods and reagents for use in distinguishing heparin sodium of porcine origin from heparin sodium of bovine origin using quantitative polymerase chain reaction.

36 Claims, 15 Drawing Sheets

Flow Diagram for Heparin Processing

Fig. 3

Porcine Plate – SINE Primers

|   | 1 | 2 | 3 | 4 | 5 | 6 | 7 | 8 | 9 | 10 | 11 | 12 |
|---|---|---|---|---|---|---|---|---|---|----|----|----|
| A | \multicolumn{12}{c}{Porcine Genomic DNA Dilutions (Standard Curve/System Suitability)} |||||||||||
| A | 1 ng | | 0.1 ng | | 0.01 ng | | 1 pg | | 0.1 pg | | 0.01 pg | |
| B | Bovine Primer Control | | NTC - Bovine Primer | | | NTC - Porcine Primer | | | | | | |
| B | 1 ng Porcine DNA | | H₂O | | | H₂O | | | | | | |
| C | | | | | | | | | | | | |
| D | | | | | | | | | | | | |
| E | | Sample # 1 (100 x Dilution) | | | | | Sample # 2 (100 x Dilution) | | | | | |
| E | | Porcine Primer | | Bovine Primer | | | Porcine Primer | | | Bovine Primer | | |
| F | | Sample # 3 (100 x Dilution) | | | | | Sample # 4 (100 x Dilution) | | | | | |
| F | | Porcine Primer | | Bovine Primer | | | Porcine Primer | | | Bovine Primer | | |
| G | | Sample # 5 (100 x Dilution) | | | | | Sample # 6 (100 x Dilution) | | | | | |
| G | | Porcine Primer | | Bovine Primer | | | Porcine Primer | | | Bovine Primer | | |
| H | | Sample # 7 (100 x Dilution) | | | | | Sample # 8 (100 x Dilution) | | | | | |
| H | | Porcine Primer | | Bovine Primer | | | Porcine Primer | | | Bovine Primer | | |

Fig. 4A

Bovine Plate – SINE Primers

| | 1 | 2 | 3 | 4 | 5 | 6 | 7 | 8 | 9 | 10 | 11 | 12 |
|---|---|---|---|---|---|---|---|---|---|---|---|---|
| A | Bovine Genomic DNA Dilutions (Standard Curve/System Suitability and LOD) | | | | | | | | | | | |
| A | 10 ng | | 1 ng | | 0.1 ng | | 0.01 ng | | 1 pg | | 0.1 pg | |
| B | Bovine DNA Dilutions + 10 ng Porcine DNA (System Suitability and LOD) | | | | | | | | | | | |
| B | 10 ng + 10 ng | | 1 ng + 10 ng | | 0.1 ng + 10 ng | | 0.01 ng + 10 ng | | 1 pg + 10 ng | | 0.1 pg + 10 ng | |
| C | Porcine Primer Control | | NTC - Bovine Primer | | | | NTC - Porcine Primer | | | | | |
| C | 10 ng Bovine DNA | | H₂O | | | | H₂O | | | | | |
| D | | | | | | | | | | | | |
| E | Sample # 1 (100 x Dilution) | | | | | | Sample # 2 (100 x Dilution) | | | | | |
| E | Porcine Primer | | | Bovine Primer | | | Porcine Primer | | | Bovine Primer | | |
| F | Sample # 3 (100 x Dilution) | | | | | | Sample # 4 (100 x Dilution) | | | | | |
| F | Porcine Primer | | | Bovine Primer | | | Porcine Primer | | | Bovine Primer | | |
| G | Sample # 5 (100 x Dilution) | | | | | | Sample # 6 (100 x Dilution) | | | | | |
| G | Porcine Primer | | | Bovine Primer | | | Porcine Primer | | | Bovine Primer | | |
| H | Sample # 7 (100 x Dilution) | | | | | | Sample # 8 (100 x Dilution) | | | | | |
| H | Porcine Primer | | | Bovine Primer | | | Porcine Primer | | | Bovine Primer | | |

Fig. 4B

Ruminant Plate

|   | 1 | 2 | 3 | 4 | 5 | 6 | 7 | 8 | 9 | 10 | 11 | 12 |
|---|---|---|---|---|---|---|---|---|---|---|---|---|
| A | \multicolumn{12}{c}{Ruminant Genomic DNA Dilutions (Standard Curve/System Suitability)} ||||||||||||
| A | 1 ng ||| 0.1 ng ||| 0.01 ng ||| 1 pg |||
| B | Ruminant Genomic DNA Dilutions |||||| NTC-1 ||| Negative Control-1 |||
| B | 0.1 pg ||| 0.01 pg ||| H₂O ||| Porcine gDNA, 1ng |||
| C | Ruminant DNA Dilutions + 10ng Porcine gDNA (Interference Control and LOD) ||||||||||||
| C | 1 ng ||| 0.1 ng ||| 0.01ng ||| 1 pg |||
| D | Ruminant DNA Dilutions + 10ng Porcine gDNA |||||| NTC-2 ||| Negative Control-2 |||
| D | 0.1 pg ||| 0.01 pg ||| H₂O ||| Porcine gDNA, 10 ng |||
| E | |||||||||||| |
| F | Sample # 1 ||| Sample # 2 ||| Sample #3 ||| Sample # 4 |||
| G | Sample # 5 ||| Sample # 6 ||| | | | | | | |
| H | |||||||||||| |

A.                                B.

Porcine Genomic DNA Standard Curve (Range: 1 ng - 0.01 pg)

→ SYBR    E= 93.4% R^2=0.999 slope=-3.491 y-int=12...

Caprine Genomic DNA Standard Curve (Range: 1 ng - 0.01 pg)

→ SYBR    E= 91.0%  R^2=0.999  slope=-3.557  y-int=11...

Ovine Genomic DNA Standard Curve (Range: 1 ng - 0.01 pg)
+ 10 ng Porcine Genomic DNA as Interference Agent Caprine Genomic DNA Standard Curve (Range: 1 ng - 0.01 pg)
+ 10 ng Porcine Genomic DNA as Interference Agent 2% Agarose Gel Electrophoresis Results:

Discussion: The results indicate that column purification ensures the purity of a DNA sample and real-time PCR amplification efficiency. Filtration does not seem to be as important as column purification.

SEQUENCE LISTING

```
<160> NUMBER OF SEQ ID NOS: 21

<210> SEQ ID NO 1
<211> LENGTH: 23
<212> TYPE: DNA
<213> ORGANISM: Bos taurus

<400> SEQUENCE: 1
tttcttgtta tagcccacca cac                                        23

<210> SEQ ID NO 2
<211> LENGTH: 23
<212> TYPE: DNA
<213> ORGANISM: Bos taurus

<400> SEQUENCE: 2
tttctctaaa ggtggttggt cag                                        23

<210> SEQ ID NO 3
<211> LENGTH: 22
<212> TYPE: DNA
```

```
<213> ORGANISM: Sus scrofa

<400> SEQUENCE: 3
gactaggaac catgaggttg cg                                        22

<210> SEQ ID NO 4
<211> LENGTH: 20
<212> TYPE: DNA
<213> ORGANISM: Sus scrofa

<400> SEQUENCE: 4
agcctacacc acagccacag                                           20

<210> SEQ ID NO 5
<211> LENGTH: 23
<212> TYPE: DNA
<213> ORGANISM: Sus scrofa

<400> SEQUENCE: 5
gcctaaatct ccctcaatg gta                                        23

<210> SEQ ID NO 6
<211> LENGTH: 24
<212> TYPE: DNA
<213> ORGANISM: Sus scrofa

<400> SEQUENCE: 6
atgaaagagg caaatagatt ttcg                                      24

<210> SEQ ID NO 7
<211> LENGTH: 23
<212> TYPE: DNA
<213> ORGANISM: Bos taurus

<400> SEQUENCE: 7
gccatatact ctccttggtg aca                                       23

<210> SEQ ID NO 8
<211> LENGTH: 21
<212> TYPE: DNA
<213> ORGANISM: Bos taurus

<400> SEQUENCE: 8
gtaggcttgg gaatagtacg a                                         21

<210> SEQ ID NO 9
<211> LENGTH: 21
<212> TYPE: DNA
<213> ORGANISM: Ovis aries

<400> SEQUENCE: 9
ttaaagactg agcgcatgat a                                         21

<210> SEQ ID NO 10
<211> LENGTH: 24
<212> TYPE: DNA
<213> ORGANISM: Ovis aries

<400> SEQUENCE: 10
atgaaagagg caaatagatt ttcg                                      24

<210> SEQ ID NO 11
<211> LENGTH: 23
```

<210> SEQ ID NO 11
<211> LENGTH: 23
<212> TYPE: DNA
<213> ORGANISM: Sus scrofa

<400> SEQUENCE: 11
catcacactg tgttggtcat tgc                                             23

<210> SEQ ID NO 12
<211> LENGTH: 24
<212> TYPE: DNA
<213> ORGANISM: Sus scrofa

<400> SEQUENCE: 12
ctcatggata ccagtcaggt ttgt                                            24

<210> SEQ ID NO 13
<211> LENGTH: 26
<212> TYPE: DNA
<213> ORGANISM: Sus scrofa

<400> SEQUENCE: 13
cactgagaca caacaggaac tccgcc                                          26

<210> SEQ ID NO 14
<211> LENGTH: 22
<212> TYPE: DNA
<213> ORGANISM: Bos taurus

<400> SEQUENCE: 14
cggaaacgac tgaaacgact tc                                              22

<210> SEQ ID NO 15
<211> LENGTH: 24
<212> TYPE: DNA
<213> ORGANISM: Bos taurus

<400> SEQUENCE: 15
gtgtgatcct acctgactgt ctaa                                            24

<210> SEQ ID NO 16
<211> LENGTH: 24
<212> TYPE: DNA
<213> ORGANISM: Bos taurus

<400> SEQUENCE: 16
cagcagcagc agcagcagca gcag                                            24

<210> SEQ ID NO 17
<211> LENGTH: 22
<212> TYPE: DNA
<213> ORGANISM: Sus scrofa

<400> SEQUENCE: 17
gattcctctc gcatccatgc ag                                              22

<210> SEQ ID NO 18
<211> LENGTH: 20
<212> TYPE: DNA
<213> ORGANISM: Sus scrofa

<400> SEQUENCE: 18
ggtccaagtc agcactggag                                                 20

<210> SEQ ID NO 19

```
<211> LENGTH: 14
<212> TYPE: DNA
<213> ORGANISM: Sus scrofa

<400> SEQUENCE: 19
tggagtcggg cccg                                                           14

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
gactgagcga cttcactttc a                                                   21

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
ggattctcca ggcaagaaca                                                     20
```

PCR ASSAY FOR ANIMAL ORIGIN OF HEPARIN

This patent application is the national phase entry of International Application No. PCT/US2012/059918, filed Jun. 3, 2011 which is hereby incorporated by reference in its entirety.

STATEMENT REGARDING FEDERALLY SPONSORED RESEARCH OR DEVELOPMENT

None

THE NAMES OF THE PARTIES TO A JOINT RESEARCH AGREEMENT

No Joint Research Agreement.

SEQUENCE LISTING

Incorporated by reference in its entirety herein is a computer-readable nucleotide/amino acid sequence listing submitted on May 22, 2015, and identified as follows: One 3405 byte ASCII (Text) file named "720461SeqListing.txt," created Apr. 9, 2015.

STATEMENT REGARDING PRIOR DISCLOSURES BY THE INVENTOR OR A JOINT INVENTOR

None

BACKGROUND OF THE INVENTION

Heparin sodium is the sodium salt of sulfated glycosaminoglycans and is a mixture of heterogeneous molecules varying in molecular weights. It is commonly used as an anticoagulant in many therapeutic and diagnostic applications. First isolated from canine liver cells in 1916, heparin is widely conserved among species and has been found in mammals as well as invertebrates. However, heparin is most commonly isolated from porcine or bovine intestinal mucosa. Despite sharing a name, porcine and bovine molecules designated as heparins have a variety of structural and functional differences. Additionally, bovine-derived heparin is associated with concerns regarding excessive bleeding as well as possible contamination with pathogens such as bovine spongiform encephalopathy. As a result, for therapeutic purposes, only porcine heparin is accepted by United States and European pharmacological authorities.

New methods are therefore needed for conclusively determining the bovine or porcine origin of crude heparin sodium.

BRIEF SUMMARY OF THE INVENTION

The invention provides methods for identifying biological contaminants in a crude heparin sample, wherein the biological contaminant is comprised of contaminant DNA of a unique sequence, the method comprising: (a) isolating DNA from the crude heparin sample, said isolating comprising: (i) simultaneously binding any DNA present and the heparin in the crude heparin sample to an anion exchange resin, (ii) differentially eluting any DNA present from the anion exchange resin with an elution solution, such that the heparin remains substantially bound to the anion exchange column, (iii), concentrating the isolated DNA, and (iv) further purifying the isolated DNA using a silica based resin such that the isolated DNA is at least 50 base pairs in length; (b) providing an aliquot of the isolated DNA to a PCR reaction mixture comprising a reporting molecule and a primer pair, wherein the primer pair is capable of selectively binding the contaminant DNA; (c) performing quantitative polymerase chain reactions on one or more aliquots of the concentrated isolated DNA extracted in step (a) using the PCR reaction mixture provided in step (b) to determine a threshold cycle (Ct) value of the sample of crude heparin; (d) calculating an average Ct value for the contaminant DNA in the crude heparin sample, wherein the average Ct value is an arithmetic mean of the Ct values determined in step (c); and (e) comparing the average Ct determined in step (d) with a standard curve of contaminant DNA concentration plotted against the Ct, wherein if the average Ct value of the sample is less than or equal to the average Ct value for a threshold level of contaminant DNA the sample is positive for the contaminant and the crude heparin sample will not be used in the manufacture of a heparin product.

Methods of determining the threshold Ct in accordance with the invention include, e.g., determining the threshold in parallel with the heparin sample and wherein the threshold Ct is based on a limit Ct determined by prior experimentation.

Suitable contaminants for detection by the inventive method include, wherein the contaminant is virus or prion, wherein the contaminant is of ruminant origin, e.g. of bovine, ovine or caprine origin.

Suitable primer pairs for use in accordance with the invention include, e.g., wherein the primers are capable of selectively binding a DNA molecule encoding a bovine or porcine SINE sequences, such as the primer pair is SEQ ID NOS: 1 and 2 for bovine DNA amplification, SEQ ID NOS: 3 and 4 for porcine DNA amplification and SEQ ID NOS: 20 and 21 for general DNA ruminant amplification, respectively.

BRIEF DESCRIPTION OF THE SEVERAL VIEWS OF THE DRAWING(S)

FIG. 1 provides a schematic diagram summarizing the process for obtaining porcine derived heparin for use as an active pharmaceutical ingredient.

FIG. 3 depicts the layout of an eight by twelve, 96 well amplification plate prepared for quantitative PCR in which porcine primers were used to amplify genomic DNA. The results were used to generate a Ct/concentration standard curve.

FIG. 4A depicts the layout of an eight by twelve, 96 well amplification plate prepared for quantitative PCR in which bovine primers were used to amplify genomic DNA. The results were used to generate a Ct/concentration standard curve.

FIG. 4B depicts the layout of an eight by twelve, 96 well amplification plate prepared for quantitative PCR in which "ruminant" primers were used to amplify genomic DNA. The results were used to generate a Ct/concentration standard curve.

Figure 5:
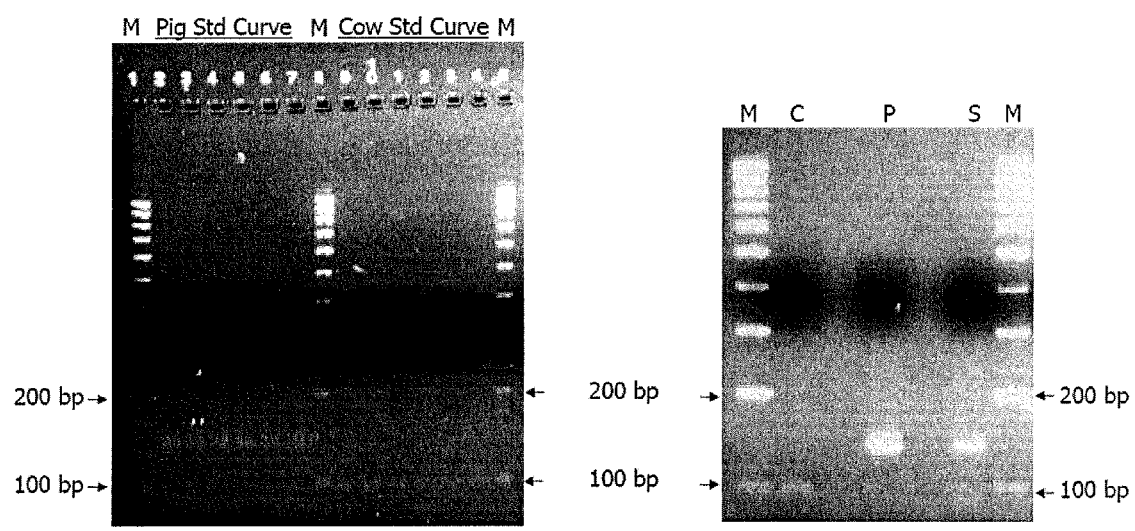

FIG. 5A provides a photograph of a 3% agarose gel on which the products of qPCR using porcine and bovine primers were run.

FIG. 5B provides an additional photograph of a 3% agarose gel on which the products of qPCR using porcine and bovine primers were run.

Figure 6:
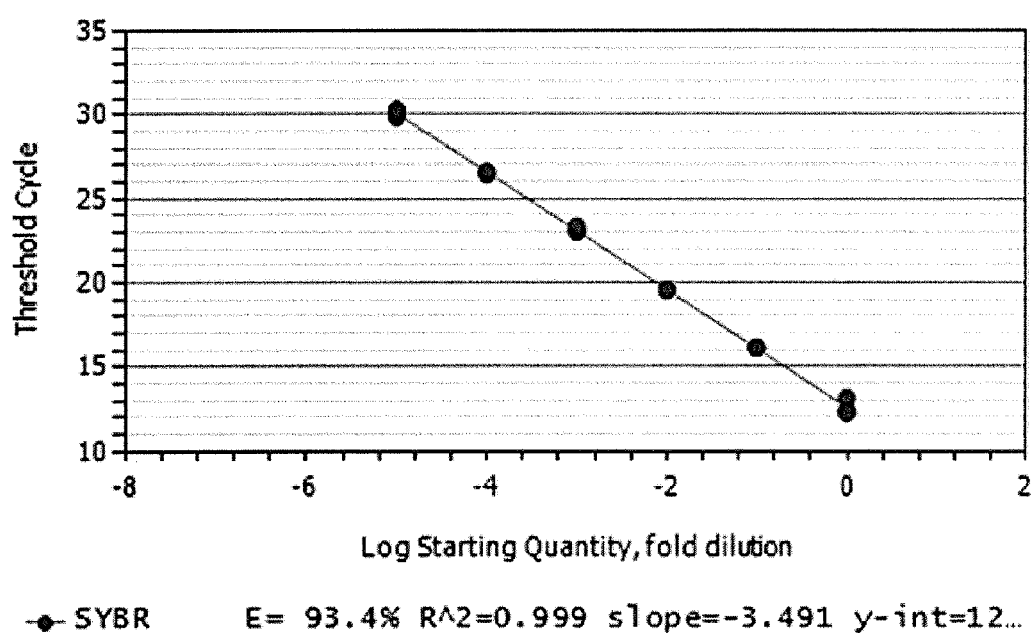

FIG. 6 depicts a Ct/concentration standard curve prepared using the qPCR results for porcine genomic DNA amplified with porcine primers.

Figure 7:
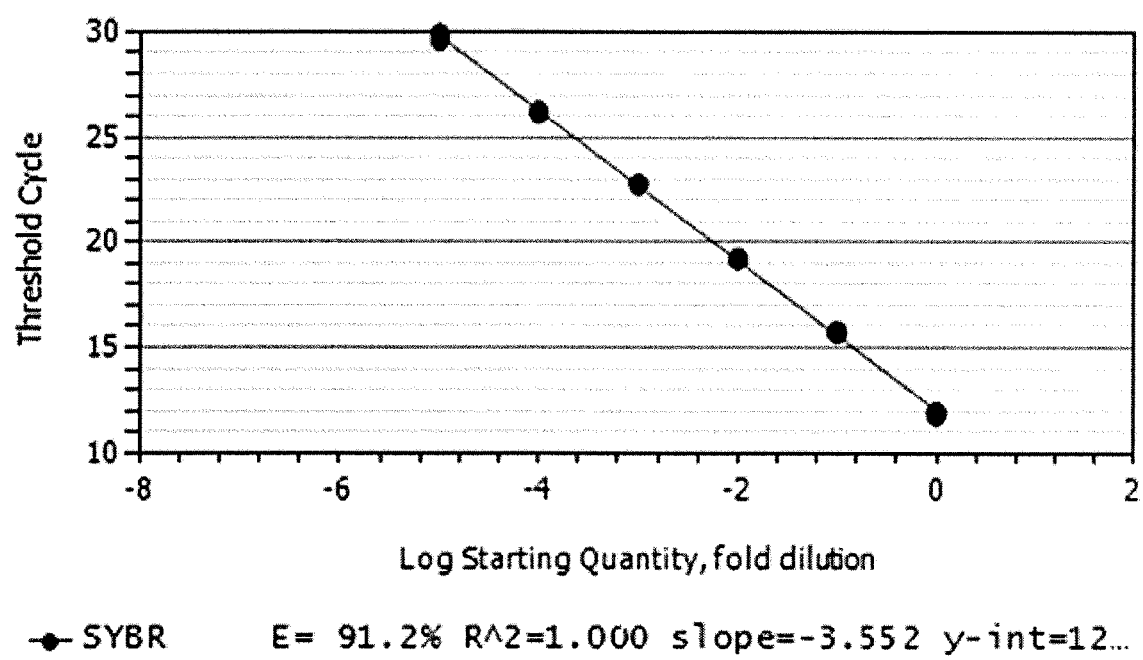

FIG. 7 depicts a Ct/concentration standard curve prepared using the qPCR results for bovine genomic DNA amplified with bovine primers.

Figure 8:
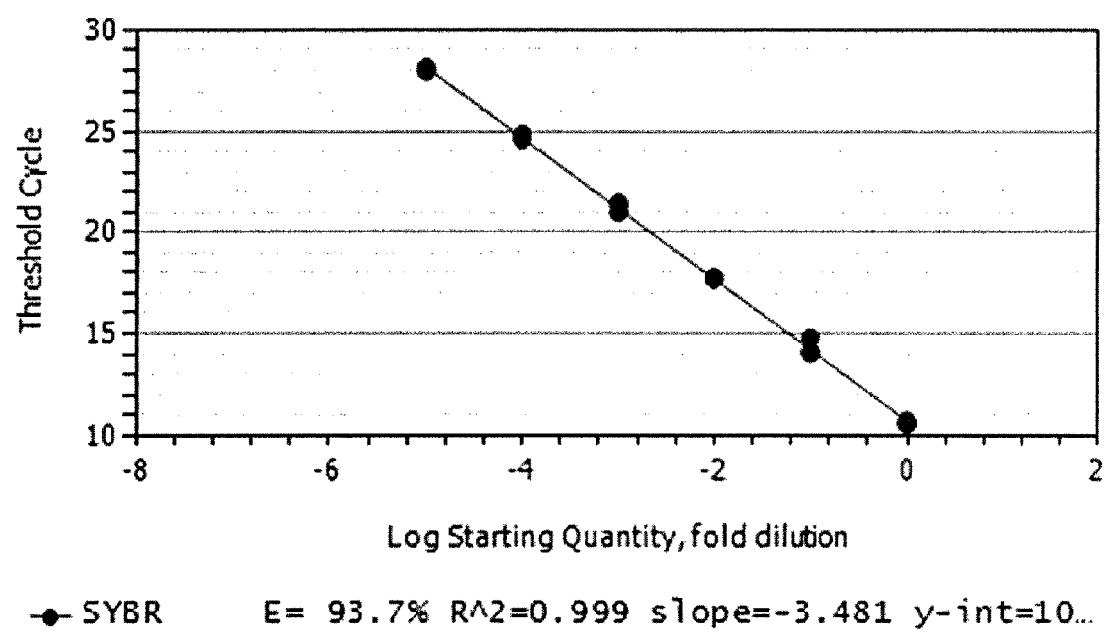

FIG. 8 depicts a Ct/concentration standard curve prepared using the qPCR results for ovine genomic DNA amplified with ovine primers.

Figure 9:
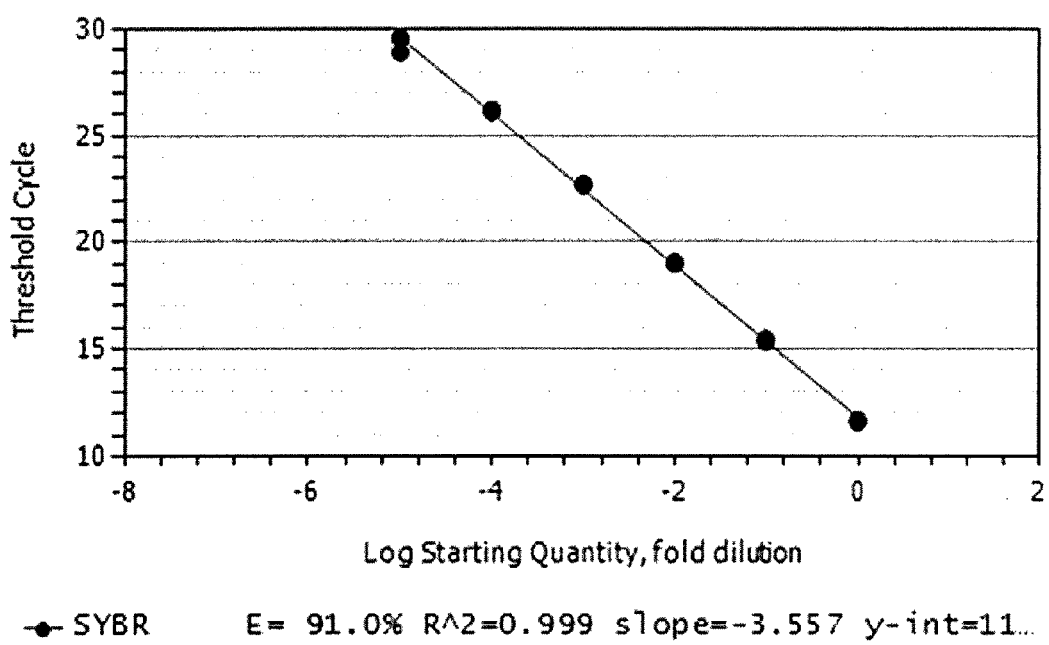

FIG. 9 depicts a Ct/concentration standard curve prepared using the qPCR results for caprine genomic DNA amplified with caprine primers.

Figure 10:
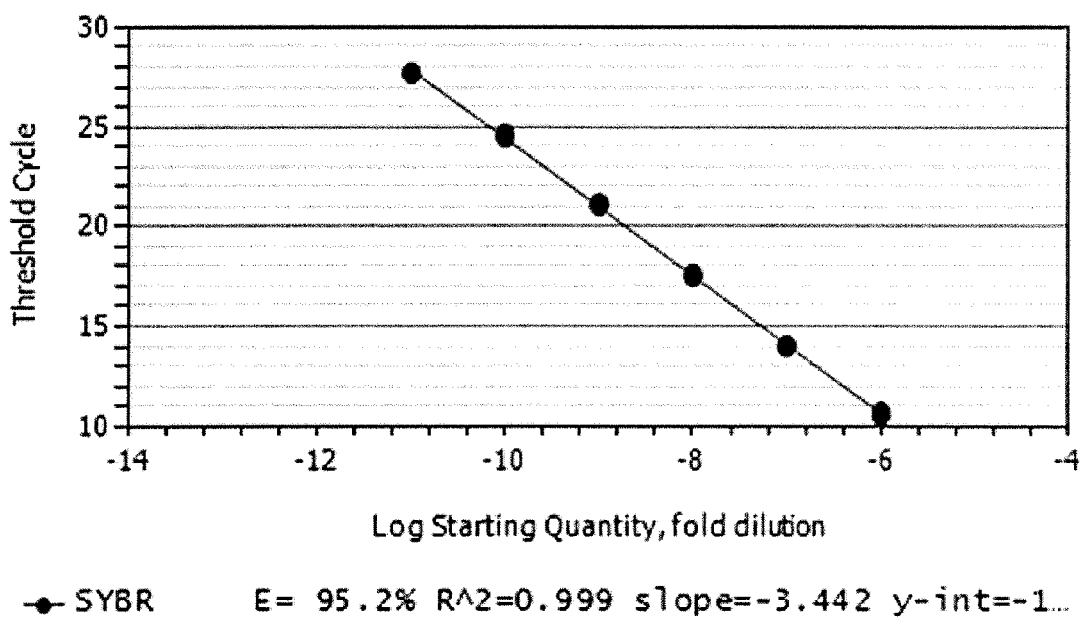

FIG. 10 depicts a Ct/concentration standard curve prepared using the qPCR results for bovine genomic DNA amplified with bovine primers in which 10 ng of porcine genomic DNA was added to the bovine genomic DNA as an interference agent.

Figure 11:
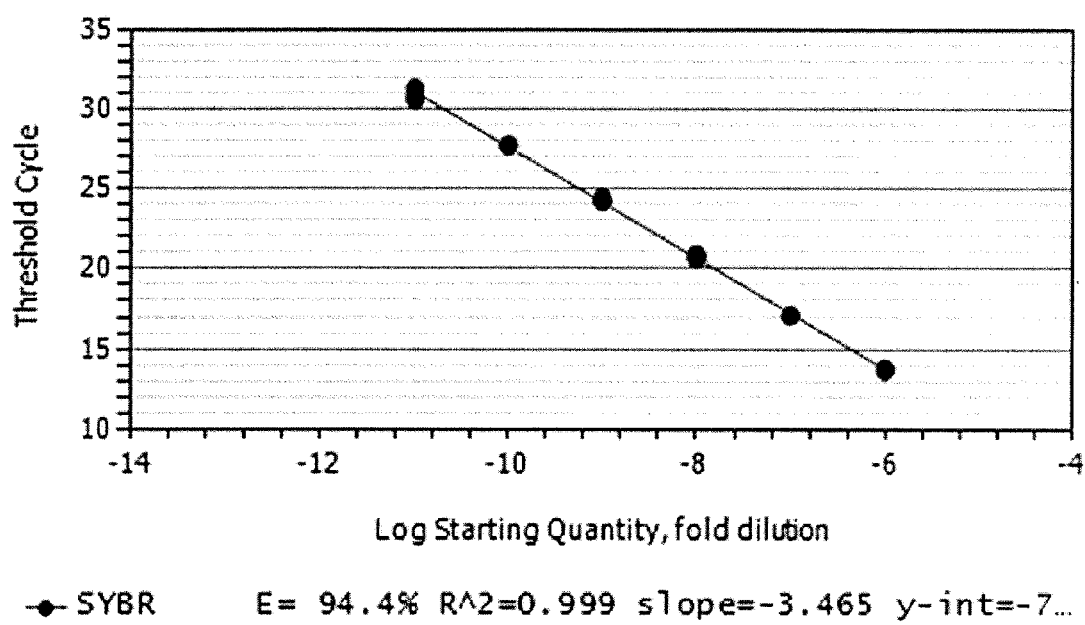

FIG. 11 depicts a Ct/concentration standard curve prepared using the qPCR results for ovine genomic DNA amplified with ovine primers in which 10 ng of porcine genomic DNA was added to the ovine genomic DNA as an interference agent.

Figure 12:
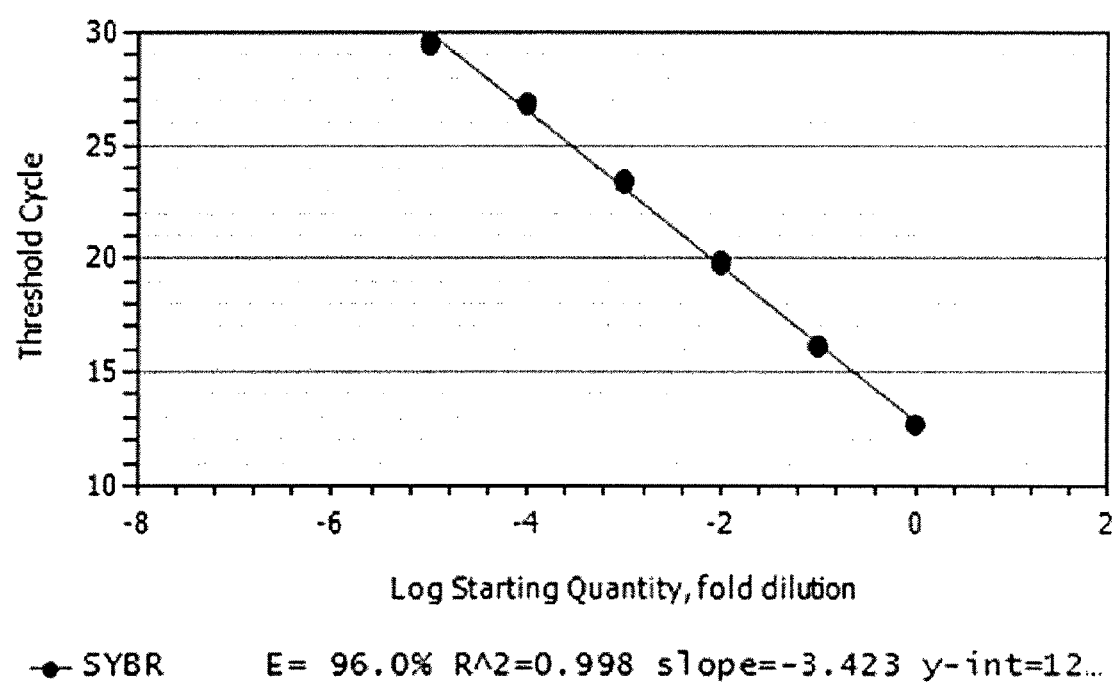

FIG. 12 depicts a Ct/concentration standard curve prepared using the qPCR results for caprine genomic DNA amplified with caprine primers in which 10 ng of porcine genomic DNA was added to the caprine genomic DNA as an interference agent.

Figure 13:
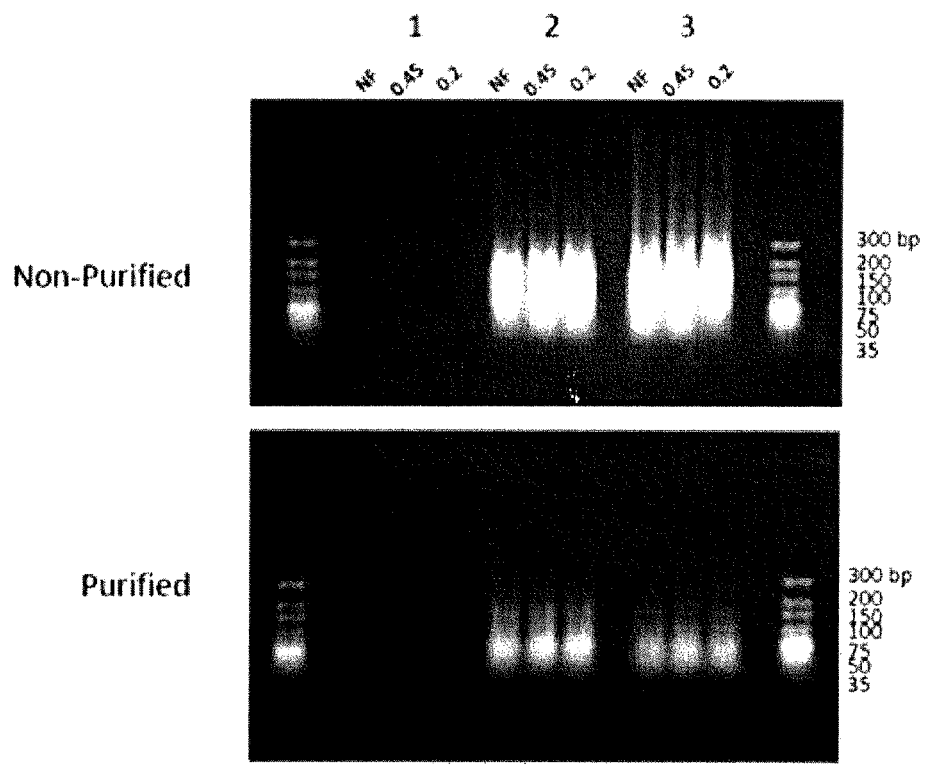

FIG. 13 depicts the result of a 2% agarose gel assay. The samples run on the gel were two aliquots of 1.0M NaCl wash samples from separate heparin lots that were subjected to either 0.45 µm or 0.2 µm filtration. A third aliquot was not filtered. Subsequently a portion of each lot was purified using the QIAquick purification kit. The purified and unpurified samples were run on agarose gels, photographs of which are provided in the figure. The results indicate that column purification is more important than filtration in obtaining pure DNA samples.

Figure 14:
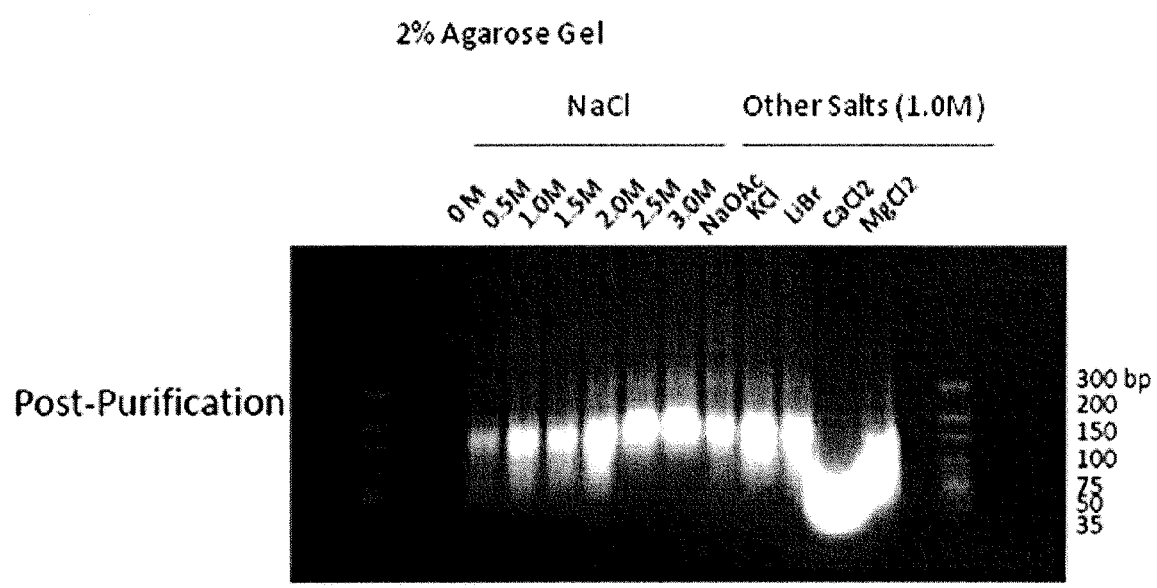

FIG. 14 depicts the result of a 2% agarose gel electrophoresis assay. The samples on the gel were obtained by washing crude heparin with various salt washes. The agarose gel shows the presence of DNA as streaks over a broad range of molecular weight of increasing intensity with increasing molarity of NaCl.

DETAILED DESCRIPTION OF THE INVENTION

The present invention provides methods and reagents for distinguishing heparin of porcine origin from heparin of bovine, ovine or other ruminant origin based on the presence of co-contaminating DNA of non-porcine origin. Heparin of porcine origin suitable for analysis according to the present invention is obtained via methods known to those skilled in the art, such as, without limitation, the process outlined in FIG. 1.

Figure 1:
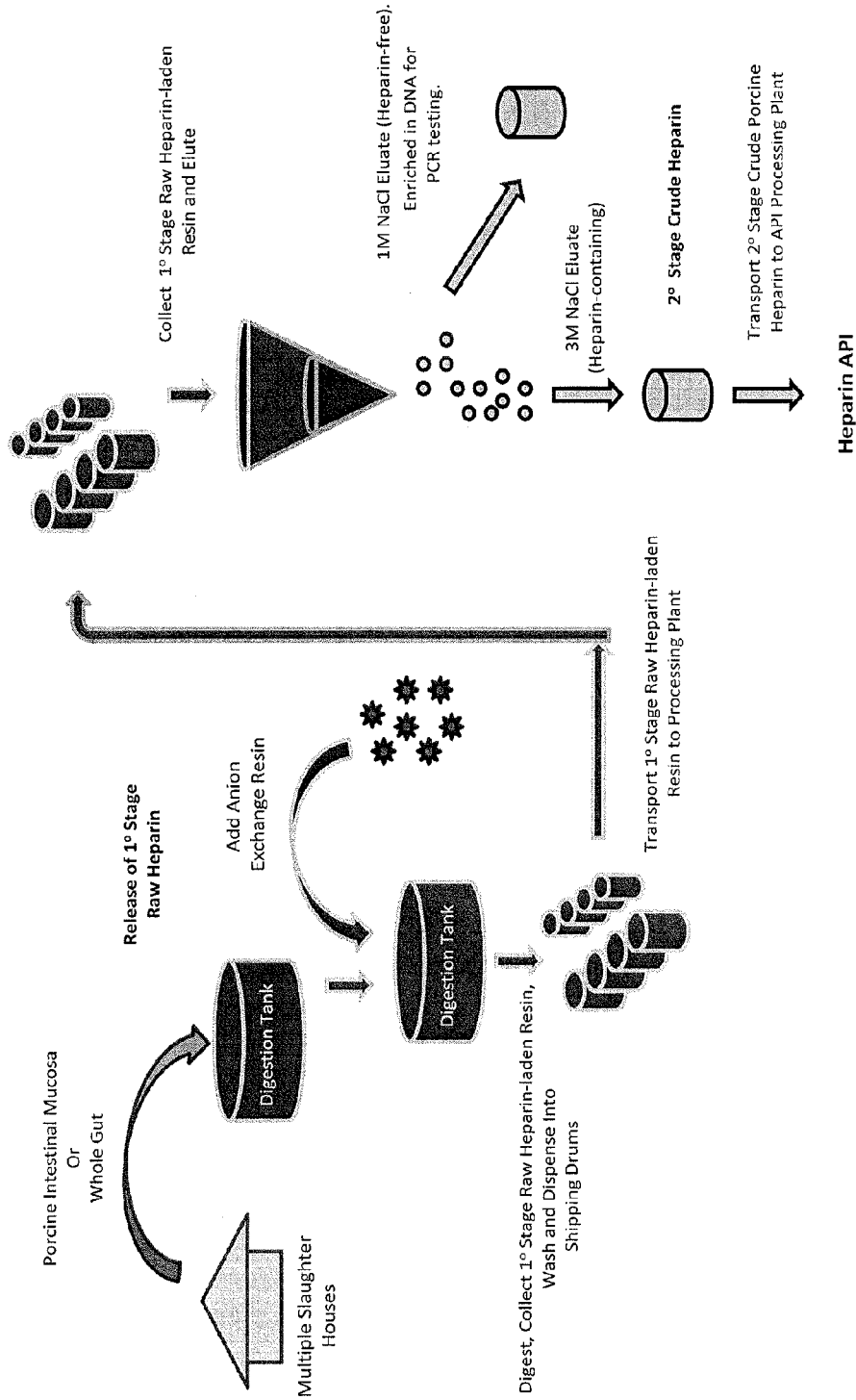

The essence of the invention is to use qPCR as a method for establishing animal origin using test articles from a point in the Heparin Process that is mapped as far upstream as possible (See FIG. 1).

It is with a high degree of difficulty to establish PCR technology in an animal slaughterhouse and the preferred site of testing for animal speciation, at the next closest point of origin, would be in a controlled laboratory setting (GxP) at the site of resin processing. (See FIG. 1). Alternatively, the present invention also provides for testing of mucosal samples which can also be taken at the early slaughterhouse stage of heparin purification.

Most commercially available material for API processing, especially from sources outside of US-based operations, is at the level of secondary ("2°") stage crude heparin extract (or "crude heparin sample") which is eluted from the anion exchange resin (See FIG. 1). Here, bulk impurities such as nucleic acids are already removed, treated with solvents and are presumably lost in the process waste-stream. Therefore, the risk of using later stage samples could leave total DNA content far below the threshold limits required to identify the presence of non-porcine DNA. Additionally, heparin-containing DNA requires the use of additional purification methods or heparinase treatment, all of which could contribute to erroneous results. Thus, PCR technology may not necessarily reflect true traceability of the animal origin when sampled at later stages of the process.

The preferred aspect of the application would be to use resin-based separation of nucleic acids from Heparin from mucosal or whole-gut digests whereby, the heparin-depleted, nucleic acid-rich fraction would be used as the test article to establish speciation and traceability. Thus, the nucleic acid fraction without further process manipulation appears to be the most representative of the mucosal/whole gut source and is an enablement to acceptance/rejection criteria.

The present invention employs nucleotide elements (SINEs) that reflect species-specific nucleotide sequences which can be measured using quantitative polymerase chain reaction (qPCR). SINEs are repetitive elements of non-coding nuclear DNA, about 100 to 500 base pairs in length, which can be found in conventionally-obtained crude heparin sodium. SINEs are well suited for use in qPCR methods because they are present in a relatively high copy number (more than $10^5$ copies per genome), so that a relatively small amount of DNA is needed. The use of SINE qPCR to identify the origin of heparin is preferable to prior methods such as oligosaccharide profiling of enoxaparin sodium, a low-molecular-weight heparin (LMWH) present in crude heparin sodium, because such non-PCR methods require more extensive preparation and suffer from a relatively great potential for inaccurate results.

Specifically, the following primers have been discovered that can be used in accordance with the invention:

```
Bovine Forward Primer,
                                SEQ ID NO: 1
5' TTTCTTGTTATAGCCCACCACAC 3';

Bovine Reverse Primer,
                                SEQ ID NO: 2
5' TTTCTCTAAAGGTGGTTGGTCAG 3';

Porcine Forward Primer,
                                SEQ ID NO: 3
5' GACTAGGAACCATGAGGTTGCG 3';

Porcine Reverse Primer,
                                SEQ ID NO: 4
5' AGCCTACACCACAGCCACAG 3';

Ruminant Forward Primer,
                                SEQ ID NO: 20
5' GACTGAGCGACTTCACTTTCA 3';
and Ruminant Reverse Primer,
                                SEQ ID NO: 21
5' GGATTCTCCAGGCAAGAACA 3'.
```

See, e.g., Walker J A, Hughes D A, Anders B A, Shewale J, Sinha S K, Batzer M A, "Quantitative intra-short interspersed element PCR for species-specific DNA identification", Analytical Biochemistry, 316 (2): 259-69 (2003) (Porcine and Bovine Primers); Luis Mendoza-Romero, Edward L. C. Verkaar, Paul H. Savelkoul, Arnold Catsburg, Henk J. M. Aarts, Jaap B. Buntjer, and Johannes A. Lenstra, "Real-time PCR detection of ruminant DNA", Journal of Food Protection 67(3): 550-554 (2004) (Ruminant Primers). As used herein, the term "a threshold level of contaminant DNA" refers to a concentration of contaminant DNA which is unacceptably high and which precludes the clinical use of the crude heparin sample from which said DNA of said concentration originated.

As used herein, the term "limit Ct" refers to a threshold Ct corresponding to a threshold of contaminant DNA.

As used herein, the term "DNA compactor" refers to compound which facilitates the amplification of DNA by effectively increasing its concentration.

The invention provides a method for distinguishing crude heparin sodium of porcine origin from heparin sodium of non-porcine origin in a sample of crude heparin sodium. The present invention can identify specimens contaminated with ruminant, e.g., bovine heparin, by detecting co-contaminating bovine DNA, the method comprising: (a) differentially eluting genomic DNA from the sample of crude heparin sodium; (b) providing a composition comprising a reporter molecule and a primer pair wherein the primer pair is capable of selectively binding a DNA molecule encoding a short interspersed nuclear element (SINE) of bovine genomic DNA; (c) performing quantitative polymerase chain reaction (qPCR) on one or more aliquots of the genomic DNA extracted in step (a) using the composition provided in step (b) to determine a threshold cycle (Ct) value of the sample; (d) calculating an average Ct value for the sample, wherein the average Ct value is an arithmetic mean of the Ct values determined in step (c); and (e) comparing the average Ct value determined in step (d) with a known bovine genomic DNA standard curve, wherein if the average Ct value of the sample is greater than or equal to the highest average Ct value of the bovine genomic DNA standard curve, the sample is bovine negative, and wherein if the average Ct value of the sample is less than the average Ct value of the bovine genomic DNA standard curve, the sample is bovine positive.

The present invention can also identify the presence of crude heparin of porcine origin, by detecting co-contaminating bovine DNA with the further steps of (f) providing a composition comprising a reporting molecule and a primer pair, wherein the primer pair is capable of selectively binding a DNA molecule encoding a SINE of porcine heparin sodium; (g) performing quantitative polymerase chain reaction (qPCR) on one or more aliquots of the genomic DNA extracted in step (a) using the composition provided in step (f) to determine a threshold cycle (Ct) value of the sample; (h) calculating an average Ct value for the sample, wherein the average Ct value is an arithmetic mean of the Ct values determined in step (g); and (i) comparing the average Ct value determined in step (h) with a porcine genomic DNA standard curve, wherein if the average Ct value of the sample is greater than or equal to the highest average Ct value of the porcine genomic DNA standard curve, the sample is porcine negative, and wherein if the average Ct value of the sample is less than the average Ct value of the porcine genomic DNA standard curve, the sample is porcine positive.

The invention further provides a primer pair for use in detecting heparin sodium of porcine origin comprising SEQ ID NOS: 3 and 4, and a primer pair for use in detecting heparin sodium of bovine origin comprising SEQ ID NOS: 1 and 2. Optionally, other contaminant DNAs can be similarly detected using appropriate primers directed to SINE sequences of, e.g., ovine origin. Any suitable qPCR protocol and any suitable qPCR reaction mix can be used in accordance with the invention.

In some preferred embodiments, the reporting molecule is a fluorescent reporter capable of selectively binding a double-stranded DNA molecule during qPCR. For example, the reporter molecule can be a SYBR Green reporter or another double-strand specific dye known to one of ordinary skill in the art. In other embodiments, the reporting molecule can be any reporter capable of selectively binding a double-stranded DNA molecule during qPCR, or a suitable sequence-specific reporting molecule. In still other embodiments of the invention the reporting molecule is a nucleic acid probe such as a TaqMan probes, Molecular Beacons, and Scorpion oligonucleotide.

Methods in accordance with the invention for qPCR include those which also employ a DNA compactor, such as hexamine cobalt, and wherein a PCR enhancer is added to the isolated DNA prior to qPCR. Suitable PCR enhancers for use in accordance with the invention include BSA, betaine, BSA, T4 phage gp32, and proteinase inhibitors.

The qPCR analysis of steps (c) and/or (g) can be repeated as many times as analytically appropriate or convenient. For example, in some embodiments, it may be appropriate to perform qPCR on at least two aliquots of the genomic DNA. In other embodiments, at least 3, 4, 5, 6, 7, 8, 9, 10, or more than 10 aliquots can be assayed and averaged. However, in preferred embodiments, the analysis of steps (c) and/or (g) are repeated at least three times each. Additionally, it will be understood that repetitions of steps (c) and/or (g) can be executed sequentially or simultaneously (e.g., in separate wells of a single PCR plate) for a particular sample.

To ensure that assays appropriately reflect the origin of a sample, one or more control assays can be performed. Any suitable qualitative PCR control known to one of ordinary skill in the art can be used. Preferred control assays include qPCR analysis of porcine or bovine genomic DNA, which may be used to develop a Standard Curve for each assay; a species specificity control (porcine DNA with bovine primers or bovine DNA with porcine primers); and a "No Template Control" (NTC) using water without DNA. For each control, the resulting curve or Ct value desirably meets minimum requirements. For example, if the species specificity control or NTC average Ct value is not greater than 0.1 pg of the genomic DNA in the appropriate standard curve (porcine or bovine), then the assay should be repeated.

Data analysis and acceptance criteria for the methods of the present invention will be understood by those of ordinary skill in the art. For either the porcine or bovine PCR assay, the cycle threshold values (Ct values) of the dilutions of the standard curve should preferably be in the range of 7-33. The threshold level can be adjusted manually for this purpose. In some embodiments, however, Ct values can range from 7-30, preferably, from 11-27, more preferably, 14-25. Preferably, there should be a 3.3 increase in the Ct value from one concentration to the next, 10×, lower concentration. In other embodiments, there is a 3.0 increase in the Ct value, or an increase of 2.8, 2.7, 2.6, or 2.5.

The $r^2$ of the standard curve is preferably greater than 0.95, although in some embodiments it is sufficient for the $r^2$ to be greater than 0.99, preferably greater than 0.95, more preferably greater than 0.90, or even more preferably greater than 0.88. Under preferred conditions, the limit of detection for bovine genomic DNA is 10 ppm (1 pg/100 ng), although higher or lower limits of detection may be achieved under varying assay conditions, as described below.

After performing the qPCR assay(s) of the present invention, a determination can be made regarding the speciation (origin) of a sample. In particular, if a sample is considered bovine negative by both porcine and bovine PCR plates, the sample can be deemed bovine negative. Similarly, e.g., if a sample is considered bovine positive by both porcine and bovine plates, the sample may be deemed bovine positive. If the results of the bovine and porcine assay are not consistent, one or both assays should be repeated. In some embodiments, it may also be preferred to repeat one or both assays in order to ensure accuracy. For example, a sample that appears to be bovine positive may advantageously be re-tested for one or both plates to confirm the bovine positive results.

A determination of whether a sample is porcine or non-porcine (i.e., bovine) in origin, is based on average cycle threshold values (Ct values) of samples after executing the qPCR assays as described herein. In one preferred embodiment, when considering a bovine assay, if the average Ct value of a sample amplified by bovine primers is less than or equal to the average Ct value of the 1 pg bovine genomic DNA in the Standard Curve, the sample is considered bovine positive at a detection limit (LOD) of 10 ppm (1 pg/100 ng). In other embodiments, when the average Ct value is less than or equal to the average Ct value for a different dilution of bovine genomic DNA in the Standard Curve, the detection limit can be higher (e.g., 12 ppm, 15 ppm, 20 ppm, 25 ppm, or 30 ppm, and intervening values) or lower (e.g., 8 ppm, 5 ppm, 3 ppm, 2 ppm, 1 ppm, 0.5 ppm, and intervening values). If the average Ct values of the negative (water) controls run with both porcine and bovine primers are both greater than the average Ct value of the 0.1 pg bovine genomic DNA in the Standard Curve, and the average Ct value of a sample amplified by bovine primers is greater than the average Ct value of the 0.1 pg bovine genomic DNA in the Standard Curve, the sample may be considered bovine negative at limit of detection ("LOD") of 1 ppm (0.1 pg/100 ng). Likewise, if the average Ct value of a sample is greater than or equal to the average Ct value of the NTC by bovine primer, the sample is considered bovine negative. Conversely, if the average Ct value of a sample amplified by bovine primers is greater than the average Ct value of the 1 pg bovine genomic DNA in the Standard Curve, the sample is considered bovine negative at an LOD of 10 ppm (1 pg/100 ng). As before, the limit of detection will be understood to vary with the concentration of DNA in the Standard Curve.

In another preferred embodiment, when considering a porcine assay, if the average Ct value of a sample amplified by porcine primers is less than or equal to the average Ct value of the 1 pg porcine genomic DNA in the Standard Curve, the sample is considered porcine positive at a LOD of 10 ppm (1 pg/100 ng). In other embodiments, when the average Ct value is less than or equal to the average Ct value for a different dilution of porcine genomic DNA in the Standard Curve, the detection limit can be higher (e.g., 12 ppm, 15 ppm, 20 ppm, 25 ppm, or 30 ppm, and intervening values) or lower (e.g., 8 ppm, 5 ppm, 3 ppm, 2 ppm, 1 ppm, 0.5 ppm, and intervening values). If the average Ct values of the negative (water) controls run with both porcine and bovine primers are both greater than the average Ct value of the 0.1 pg porcine genomic DNA in the Standard Curve, and the average Ct value of a sample amplified by bovine primers is greater than the average Ct value of the 0.1 pg porcine genomic DNA in the Standard Curve, the sample may be considered porcine negative at LOD of 1 ppm (0.1 pg/100 ng).

If the average Ct value of a sample amplified by porcine primers is greater than the average Ct value of the 0.1 pg porcine genomic DNA in the Standard Curve, the assay is optionally repeated at least once with a different resin sample from the same batch. If upon completion of a predetermined number of repeat assays, such as three, two, one or zero repeat assays, the average Ct value of the repeat sample probed by the porcine primer is still more than the average Ct value of the 0.1 pg porcine genomic DNA in the Standard Curve, the batch of resin is not porcine positive.

In another embodiment, the invention provides a primer pair for use in detecting heparin sodium of porcine origin comprising SEQ ID NOS: 3 and 4, and a primer pair for use in detecting heparin sodium of bovine origin comprising SEQ ID NOS: 1 and 2.

In another embodiment, the invention provides for the testing of crude mucosal extracts, from which DNA can be extracted by any suitable method known to those of ordinary skill in the art, including, without limitation, methods with or without any one of homogenization and/or chemical extraction and/or enzymatic digestion.

Prior efforts to employ quantitative PCR for determination of the origin of heparin have been hindered by heparin's tendency to inhibit PCR. However, the methods of the present invention allow qPCR to be executed at a high sensitivity, using a relatively small sample. Additionally, heparinase digestion is not necessary in the methods of the present invention.

Preferably, the sample of crude heparin sodium is provided in a resin-bound form. However, in other embodiments, the heparin sodium can be provided in any suitable form known to those of ordinary skill in the art or conventionally produced by suppliers of crude heparin sodium. Any method of preparing the crude heparin can be used in accordance with the invention.

The invention provides for methods of isolating DNA from the crude heparin sample, said isolating comprising: (i) simultaneously binding any DNA present and the heparin in the crude heparin sample to an anion exchange resin, (ii) differentially eluting any DNA present from the anion exchange resin with an elution solution, such that the heparin remains substantially bound to the anion exchange column, and (iii), concentrating the isolated DNA, and (iv) further purifying the isolated DNA using a silica based resin such that the isolated DNA is at least 50 base pairs in length, e.g., where the silica resin is a QIAquick column.

Methods in accordance with the invention include, e.g., wherein the isolating further comprises a filtration step after step (ii) and before step (iii), wherein said filtration step uses a 0.45 μm pore size filter.

Any suitable heparin binding anion exchange resin may be used in accordance with the invention, including, e.g., where the resin is an Amberlite resin (Rohm and Haas Co., Philadelphia, Pa.). Suitable elution solutions for use in accordance with the invention can be selected from the group consisting of aqueous solutions of sodium acetate, potassium chloride, magnesium chloride, calcium chloride, lithium bromide and sodium chloride. In a preferred embodiment the resin elution solution is from about 1.0 M to about 2.0 M sodium chloride, in particular where the elution solution comprises about 1.0 M sodium chloride.

Methods in accordance with the invention result in the isolated DNA having a heparin concentration of less than 70 IU/mL, preferably less than 50 IU/mL, more preferably less than 40 IU/mL.

The following examples further illustrate the invention but, of course, should not be construed as in any way limiting its scope.

Example 1

This example demonstrates the design of SINE primers which can be used in differentiating heparin sodium of porcine origin from that of bovine origin.

Figure 2:
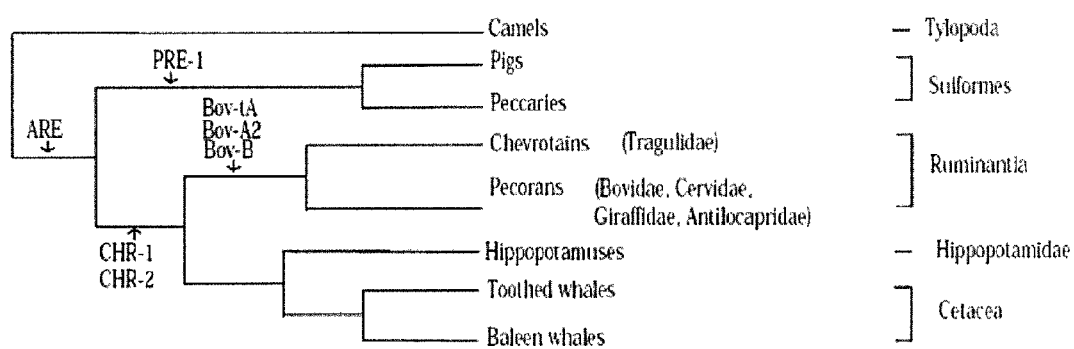
FIG. 2 depicts the relationship between SINEs in different species, which were considered in the design of SINE primers which are used in the present invention in differentiating heparin sodium of porcine origin from that of bovine origin.

Genomic nucleotide sequences encoding porcine and bovine heparin sodium were reviewed to identify SINEs. The putative SINEs analyzed included poly(A) stretches and insertion duplication sites and this analysis took into consideration the relationship between SINEs in different species (FIG. 2). Inter-species homology was evaluated to rule out SINEs conserved among porcine and bovine species. SINEs selected for further review included previously identified porcine SINE PRE-1 and bovine 1.711B Bovine Repeat. In designing appropriate primers, homology to other SINE-containing sequences in the genome was also considered.

Amplification plates were set up as shown (FIGS. 3 and 4), qPCR was performed, and the products run out on a 3% agarose gel (FIG. 5A.) The qPCR results were used for the generation of Ct/concentration standard curves for the porcine and bovine primers. Features of these standard curves are provided in Table 1.

TABLE 1

Primer Standard Curve Characteristics

| Species | Forward Primer | Reverse Primer | 10× Dilutions (6) | Ct Values | $R^2$ | Amplification Efficiency |
|---|---|---|---|---|---|---|
| Cow | SEQ ID NO: 1 | SEQ ID NO: 2 | 10 ng-0.1 pg | 10-30 | >0.98 | 90%-110% |
| Pig | SEQ ID NO: 3 | SEQ ID NO: 4 | 1 ng-0.01 pg | 10-30 | >0.98 | 90%-110% |

Agarose gel electrophoresis analysis (FIG. 5B) demonstrated that the porcine primer pair provided a PCR amplicon size of 134 base pairs ("bp") from genomic DNA, although 171 bp and 85 bp fragments resulted when analyzed with respect to a sample DNA The bovine primer pair provided a PCR amplicon size of 98 bp. Porcine and bovine specificity were confirmed by BLAST analysis (e.g., see www.blast.ncbi.nm.nih.gov).

These results show that primers having SEQ ID NOS: 1 and 2 and 3 and 4 are suitable for identifying the presence of and differentiating porcine and bovine DNA, respectively.

Example 2

This example demonstrates a method of determining whether a sample of crude heparin sodium is of porcine or bovine origin.

A 3 g sample of crude heparin bound resin from each of six samples obtained from a slaughter house were weighed and mixed with 3 mL 1M NaCl solution at a 1:1 ratio, and incubated at room temperature for at least one hour. The resulting mixture was filtered using a syringe filter to remove debris. Further purification was then performed using a commercially available polymerase chain reaction (PCR) purification kit (e.g., QIAquick, Qiagen, Germantown, Md.), which includes a spin column for centrifugation. Concentration of the purified DNA (A260 nm) was determined using standard spectroscopy methods and commercially available software for the relevant calculations (Bio-Rad iQ5 Real Time PCR Detection System, BioRad, Hercules, Calif.). The purified DNA was diluted to an absorbance between 0.1 and 1.0, with a ratio of A260/A280 between 1.8 and 2.0. DNA concentration was determined, with repeated spin column purification or dilution with 1M NaCl as necessary until a target DNA concentration of 100-1000 µg/mL was reached.

To prepare a testing sample for use in evaluating the presence of porcine and bovine origin Heparin Sodium, 1 ng/µL solution for each sample was prepared by diluting the sample with DNase/RNase free water based on the A260 value.

To prepare a pooled sample for use in evaluating the presence of bovine origin Heparin Sodium, equal volumes of multiple testing samples were prepared to obtain a final concentration of 25 ng/µL for the pooled sample, with minimum volume of 100 µL.

Porcine and bovine genomic DNA working stock solutions (10 ng/µL) were obtained by diluting commercially available porcine or bovine genomic DNA with DNase/RNase free water.

Primer stock solutions (100 pmol/µL) for each primer (SEQ ID NOs: 1 and 2 and 3 and 4, respectively) were prepared by reconstituting each with DNase/RNase free water based on the amount nmol of primer stated on the Certificate of Analysis (COA). Primer working solutions (10 pmol/µL) were prepared by diluting primer stock solution (100 pmol/µL) with DNase/RNase free water.

To perform a PCR assay to evaluate the presence of porcine origin Heparin Sodium, a PCR plate was prepared with positive controls (porcine genomic DNA, dilutions ranging from 0.2 ng/µL to 0.002 pg/µL), species specificity controls (highest concentration of porcine standard curve dilution, with bovine primers), negative (water) control, and test samples (5 µL (5 ng) of each 1 ng/µL, sample dilution).

To execute a PCR assay to evaluate the presence of bovine origin Heparin Sodium, a PCR plate was prepared with positive controls (bovine genomic DNA, dilutions ranging from 0.2 ng/µL to 0.002 pg/µL), sample DNA interference controls (4 µL of the 25 ng/µL pooled sample), species specificity controls (highest concentration of bovine standard curve dilution, with porcine primers), negative (water) control, and test samples (5 µL (5 ng) of each 1 ng/µL sample dilution). FIGS. 3 and 4 provide schematic representations of the various test and control samples analyzed on such plates.

For each PCR requiring porcine primers, a 15 µL aliquot of SYBR Green mix with porcine primers was prepared containing 10 µL of SYBR Green Supermix (2×), 0.3 of porcine forward primer (SEQ ID NO: 3) working solution (10 pmol/µL), 0.3 µL of porcine reverse primer (SEQ ID NO: 4) working solution (10 pmol/µL), and 4.4 µL of DNase/RNase free water. The final concentration of SYBR Green was 1×, with each primer at 150 nM, in a total volume of 20 µL (including 5 µL of DNA/water) for each reaction. 15 µL of SYBR Green mix with porcine primers was added to each well for porcine primer amplification. For each PCR requiring bovine primers, except the DNA interference control, identical SYBR Green mix was prepared with bovine primers (SEQ ID NO: 1 and 2) in place of the porcine primers.

For the DNA interference control of the bovine PCR plate, an 11 µL aliquot of SYBR Green mix with bovine primers (SEQ ID NO: 1 and 2) was prepared with 10 µL of SYBR Green Supermix (2×), 0.3 µL of bovine forward primer working solution (10 pmol/μL), 0.3 μL of bovine reverse primer working solution (10 poml/μL), and 0.4 μL of DNase/RNase free water.

The PCR plates were sealed. The plates were inserted into the PCR apparatus which was operated according to manufacturers' instructions. (Bio-Rad iQ5 Real Time PCR Detection System, BioRad, Hercules, Calif.). Standard curves and cycle threshold (Ct) values were generated using commercially available software.

For the six tested samples, Ct values of the dilutions of the standard curve were 11-29 for the porcine plate and 10-31 for the bovine plate, each of which was within the acceptable range of 7-33. Graduated dilutions exhibited appropriate increase in Ct value from one concentration to the next 10× lower concentration, providing an $r^2$ of 1.00 for both the porcine and bovine standard curves. Likewise, the Ct value range for sample interference control was 10-32, with an $r^2$ of 1.00 and a LOD of 10 ppm.

Plate specificity for the porcine plate indicated a Ct value of 25 for the 0.1 pg porcine genomic DNA, with values of 35 for the remaining controls (bovine and porcine non-template controls and species specificity control). Plate specificity for the bovine plate indicated similar results with a Ct value of 27 for the 0.1 pg bovine genomic DNA, with values of 35 for bovine and porcine non-template controls and a value of 33 for the species specificity control.

Amplification results for the six samples are presented in Table 2 below for time zero and at one week.

TABLE 2

Amplification Results

| Sample ID | Porcine Primer Amplification (Ct) | | Bovine Primer Amplification (Ct) | |
|---|---|---|---|---|
| | Time (0) | Time (1 week) | Time (0) | Time (1 week) |
| 129 (5x) | 15 | 17 | 35 | 35 |
| 129 (10x) | 16 | N/A | 35 | N/A |
| 184 | 19 | 21 | 35 | 35 |
| 252 | 13 | 14 | 35 | 35 |
| 285 (5x) | 14 | 15 | 35 | 35 |
| 285 (10x) | 14 | N/A | 35 | N/A |
| 332 (5x) | 14 | 15 | 35 | 35 |
| 332 (10x) | 14 | N/A | 35 | N/A |
| 339 (5x) | 32 | N/A | 35 | N/A |
| 339 (10x) | 31 | 35 | 35 | 35 |
| 339 (Repeat 5x) | 35 | N/A | 35 | N/A |
| 339 (Repeat 10x) | 35 | N/A | 35 | N/A |

Speciation results for the six samples are presented in Table 3, below.

TABLE 3

Speciation

| Sample ID | Porcine Origin | | Bovine Origin | |
|---|---|---|---|---|
| | Time (0) | Time (1 week) | Time (0) | Time (1 week) |
| 129 | Yes | Yes | No | No |
| 184 | Yes | Yes | No | No |
| 252 | Yes | Yes | No | No |
| 285 | Yes | Yes | No | No |
| 332 | Yes | Yes | No | No |
| 339 | No | No | No | No |

As shown in Table 3, samples 129, 184, 252, 285, and 332 were found to be porcine positive and bovine negative. Despite repetition of the analysis of sample 339, the sample could not be confirmed to be porcine positive, i.e., its Ct values for porcine primers (32 for the 5× sample and 31 for the 10× sample, with values of 35 for both 5× and 10× samples of the repeated assay) did not meet the acceptance criteria based on the porcine genomic DNA standard curve range.

These results show that methods in accordance with the invention can be used to determine the species of origin of a crude heparin sample.

Example 3

This example presents standard curves prepared as described in EXAMPLE 2 with genomic DNA from various species.

Standard curves were prepared using genomic DNA from four species according to the methods previously described and were compared with one another. An exemplary standard curve prepared with porcine genomic DNA is presented in FIG. 6. An exemplary standard curve prepared with Bovine genomic DNA is presented in FIG. 7. An exemplary standard curve prepared with ovine genomic DNA is presented in FIG. 8. An exemplary standard curve prepared with caprine genomic DNA is presented in FIG. 9. A comparison of these curves demonstrates the high level of reproducibility achieved with the inventive methods. Particularly, the slope of the curves obtained across the four species are highly similar. Table 4 presents theses slopes, indicating similar efficiencies.

TABLE 4

Standard Curve Characteristics

| Species Origin | Slope |
|---|---|
| Porcine | −3.491 |
| Bovine | −3.552 |
| Ovine | −3.481 |
| Caprine | −3.557 |

The amplified DNA was gel purified and sequenced. The results verified the specificity of amplification.

Additional standard curves were prepared using genomic bovine, ovine and caprine DNA spiked with 10 ng porcine DNA to determine whether porcine DNA acts as an interference agent. Exemplary standard curves for porcine spiked bovine, ovine and caprine genomic DNA are presented as FIGS. 10, 11 and 12, respectively. These curves demonstrate the same high level of consistency as the unspiked standard curves. The slopes for these curves are presented in Table 5 below.

TABLE 5

Slopes

| Bovine | −3.442 |
|---|---|
| Ovine | −3.465 |
| Caprine | −3.423 |

Thus, this example demonstrates that the effectiveness of methods of standard curve preparation described herein are highly consistent across species and further shows that porcine DNA does not interfere with the amplification of non-porcine DNA.

Example 4

This example demonstrates that numerous primer sets for the amplification of genomic DNA that were unexpectedly and surprisingly found to be unsuitable for use in the inventive methods.

Table 6 lists the primers/primer pairs which were unsuitable.

TABLE 6

Inoperative Primers

Target sequence: Mitochondrial DNA

Lahiff S., Glennon M., O'Brien L., Lyng J., Smith T., Maher M., Shilton N., "Species-specific PCR for the identification of ovine, porcine and chicken species in meta and bone meal (MBM)", Mol Cell Probes. 2001 Feb: 15(1):27-35.

| | |
|---|---|
| Porcine Forward: | 5'-GCCTAAATCTCCCCTCAATGGTA (SEQ ID NO. 5) |
| Porcine Reverse: | 5'-ATGAAAGAGGCAAATAGATTTTCG (SEQ ID NO. 6) |
| | LOD: 1% |
| Bovine Forward: | 5'-GCCATATACTCTCCTTGGTGACA (SEQ ID NO. 7) |
| Bovine Reverse: | 5'-GTAGGCTTGGGAATAGTACGA (SEQ ID NO. 8) |
| | LOD: 1% (S. Lahiff, et al.) |
| Ovine Forward: | 5'-TTAAAGACTGAGCGCATGATA (SEQ ID NO. 9) |
| Ovine Reverse: | 5'-ATGAAAGAGGCAAATAGATTTTCG (SEQ ID NO. 10) |
| | LOD: 5% |

Houiste C., Auguste C., Anger P., Brin J.F., "Quantitative PCR and Disaccharide Profiling to Characterize the Origin of Low Molecular Weight Heparin", The FASEB Journal. 2007:21:1b419

| | |
|---|---|
| Porcine Forward: | 5'-CATCACACTGTGTTGGTCATTGC (SEQ ID NO. 11) |
| Porcine Reverse: | 5'-CTCATGGATACCAGTCAGGTTTGT (SEQ ID NO. 12) |
| Probe (Reverse): | 5'-CACTGAGACACAACAGGAACTCCGCC (SEQ ID NO. 13) |
| Bovine Forward: | 5'-CGGAAACGACTGAAACGACTTC (SEQ ID NO. 14) |
| Bovine Reverse: | 5'-GTGTGATCCTACCTGACTGTCTAA (SEQ ID NO. 15) |
| Probe (Forward): | 5'-CAGCAGCAGCAGCAGCAGCAG (SEQ ID NO. 16) |
| Ovine Forward: | 5'-GATTCCTCTCGCATCCATGCAG (SEQ ID NO. 17) |
| Ovine Forward: | 5'-GGTCCAAGTCAGCACTGGAG (SEQ ID NO. 18) |
| Probe (Forward): | 5'-TGGAGTCGGGCCCG (SEQ ID NO. 19) |

Example 5

This example describes experiments to determine the significance of filtration and column purification during PCR sample preparation.

Three separate, unrelated preparations of heparin bound resin were washed with 1.0 M NaCl as described above in EXAMPLE 2. Two aliquots of the 1.0M NaCl wash samples from each heparin lot were subjected to either 0.45 μm or 0.2 μm filtration. A third aliquot was not filtered. Subsequently, a portion of each aliquot was column purified using the QIAquick™ purification kit as also described in EXAMPLE 2 above. Real-time PCR was performed as previously described for all of these samples using porcine genomic DNA as a standard. The results are presented in table 7 below.

TABLE 7

Replicate Results

| 1M NaCl wash sample | Filtration | Column Purification | $A_{260}$ (Limit: 0.1-1.0) | $A_{260}/A_{280}$ (Limit: 1.8-2.2) | Ct Value (Standard Curve Range: 11-28) |
|---|---|---|---|---|---|
| Hep 122 | No filter | No | 0.1 | 1.5 | 35 |
| | | Yes | 0.4 | 1.8 | 24 |
| | 0.45 μm | No | 0.2 | 1.7 | 35 |
| | | Yes | 0.2 | 1.9 | 29 |
| | 0.2 μm | No | 0.2 | 1.5 | 35 |
| | | Yes | 0.1 | 1.8 | 25 |
| Hep 241 | No filter | No | 0.3 | 1.7 | 16 |
| | | Yes | 0.2 | 1.9 | 13 |
| | 0.45 μm | No | 0.3 | 1.7 | 15 |
| | | Yes | 0.2 | 1.9 | 13 |
| | 0.2 μm | No | 0.2 | 1.7 | 24 |
| | | Yes | 0.3 | 1.9 | 13 |
| Hep 333 | No filter | No | 0.3 | 1.8 | 16 |
| | | Yes | 0.3 | 1.9 | 11 |
| | 0.45 μm | No | 0.4 | 1.8 | 16 |
| | | Yes | 0.3 | 1.9 | 11 |
| | 0.2 μm | No | 0.4 | 1.8 | 16 |
| | | Yes | 0.2 | 1.9 | 11 |

The resultant amplified DNA for each test sample were run on 2-3% agarose gels using techniques known in the art. Images of the gels are presented as FIG. 13. The results of the gel confirm that column purification results in increased DNA sample purity and increased real-time PCR efficiency and that filtration has a lesser effect.

The results of this experiment indicate the column purification step improves both the purity of the DNA sample and real-time PCR amplification efficiency. Filtration has a lesser effect on purity and amplification efficiency.

Example 6

This example describes experiments performed to determine the DNA availability in samples prepared by washing heparin-bound resin with various salt washes. Gel electrophoresis of the salt washes tested are shown in FIG. 14 and the resulting DNA concentrations are presented in Table 8:

TABLE 8

Elution Solutions

| Salt Solution | Concentration |
|---|---|
| NaCl | 0M (SWFI) |
| | 0.5M |

TABLE 8-continued

Elution Solutions

| Salt Solution | Concentration |
|---|---|
| | 1.0M |
| | 1.5M |
| | 2.0M |
| | 2.5M |
| | 3.0M |
| NaOAc | 1.0M |
| KCl | 1.0M |
| MgCl$_2$ | 1.0M |
| CaCl$_2$ | 1.0M |
| LiBr | 1.0M |

Non-purified samples were obtained by washing the same sample of heparin-bound resin with each of these salt solutions. A heparin activity screening assay and agarose gel electrophoresis were performed on each of these eluents.

Heparin activity (described as "units" of heparin) was assessed using methods known to those skilled in the art. The results of this heparin activity screening assay for the various unpurified salt washes are presented in Table 9, below.

TABLE 9

Elution Results

| Sample Eluent | [Heparin] (U/mL) | Total Units of Heparin |
|---|---|---|
| SWFI | 0 | 0 |
| 0.5M NaCl | 0 | 0 |
| 1.0M NaCl | 62 | 372 |
| 1.5M NaCl | 2265 | 13590 |
| 2.0M NaCl | 2939 | 17634 |
| 2.5M NaCl | 3007 | 18042 |
| 3.0M NaCl | 3068 | 18408 |
| 1.0M NaOAc | 0 | 0 |
| 1.0M KCl | 488 | 2928 |
| 1.0M MgCl$_2$ | 1838 | 11028 |
| 1.0M CaCl$_2$ | 2768 | 16608 |
| 1.0M LiBr | 144 | 864 |

Based on the results of the heparin activity screening assay, the maximum concentration of heparin in any given salt solution was ~3000 U/mL and for NaCl in particular, there was no significant difference in heparin concentration beyond 2.0 M NaCl. Surprisingly, the heparin activity is significantly lower in the 1.0M wash sample than the 1.5M NaCl wash sample. Between 0.5 and 1.5M NaCl the data shows a surprisingly non-linear relationship between heparin activity and NaCl concentration. Regarding the samples obtained with other salt washes, heparin activity is significantly higher than the activity in the 0.5M and 1.0M NaCl samples, with the exception of 1.0M NaOAc These samples were also run on 2-3% agarose gels utilizing methods known in the art. A photograph of such a gel is presented as FIG. 14. The agarose gels show the presence of DNA as streaks over a broad range of molecular weight of increasing intensity with increasing molarity of NaCl. Without wishing to be bound by any particular theories, this broad distribution may be attributed to the sheared nature of the sample DNA.

The salt wash samples were then purified by using the QIAquick™ purification kit as described in EXAMPLE 2. Real-time PCR was performed with the purified salt wash samples, each purified sample was diluted to 2 ng/μL based upon its DNA concentration, and then 5 μL of each sample was used for used for real time PCR. The results are presented in Table 10, below.

TABLE 10

Further Elution Results

| Sample Eluent | A$_{260}$ (Limit: 0.1-1.0) | A$_{260}$/A$_{280}$ (Limit: 1.8-2.2) | [DNA] (ng/μL) | Ct Value (Standard Curve Range: 11-28) |
|---|---|---|---|---|
| SWFI (0M NaCl) | 0.01 | 1.7 | 3.0 | 16 |
| 0.5M NaCl | 1.0 | 1.9 | 476.5 | 12 |
| 1.0M NaCl | 0.3 | 1.9 | 618.0 | 12 |
| 1.5M NaCl | 0.3 | 1.9 | 663.2 | 13 |
| 2.0M NaCl | 0.4 | 1.9 | 724.6 | 13 |
| 2.5M NaCl | 0.3 | 1.9 | 693.1 | >31 |
| 3.0M NaCl | 0.4 | 1.9 | 720.3 | 35 |
| 1.0M NaOAc | 0.3 | 1.9 | 610.2 | 14 |
| 1.0M KCl | 0.4 | 1.9 | 714.7 | 18 |
| 1.0M LiBr | 0.3 | 1.9 | 665.7 | 12 |
| 1.0M CaCl$_2$ | 0.4 | 2.0 | 6932.4 | 15 |
| 1.0M MgCl$_2$ | 0.7 | 2.0 | 2105.2 | 13 |

Finally, a standard heparin activity assay, known to those of ordinary skill, was repeated on the purified salt wash samples. In this assay, the 2.0 M NaCl wash sample demonstrated a similar level of heparin activity as compared to the 2.5 M NaCl and 3.0 M NaCl wash samples, yet did not exhibit inhibition when tested by PCR. To investigate this result, four unpurified NaCl salt wash samples (1.5 M, 2.0 M, 2.5 M and 3.0 M) were repurified and tested by real time PCR and the results were compared with the data obtained for these washes prior to purification. This comparison was used to determine the relationship between heparin activity and PCR inhibition. Tables 11 and 12 present data for the four NaCl washes before and after purification.

TABLE 11

Ct Results at Different NaCl Concentrations

| Sample Eluent | A$_{260}$ (Limit: 0.1-1.0) | A$_{260}$/A$_{280}$ (Limit: 1.8-2.2) | [DNA] (ng/μL) | Ct Value (Standard Curve Range: 12-29) |
|---|---|---|---|---|
| 1.5M NaCl | 0.3 | 1.9 | 429.0 | 13 |
| 2.0M NaCl | 0.3 | 1.9 | 436.6 | 14 |
| 2.5M NaCl | 0.4 | 1.9 | 498.7 | 35 |
| 3.0M NaCl | 0.4 | 1.9 | 497.0 | 35 |

TABLE 12

Heparin Activity at Different NaCl Concentrations

| Sample Eluent | Heparin Activity (U/mL) Unpurified | Ct (Old) (Standard Curve Range: 11-28) | Heparin Activity (U/mL) Purified | Ct (New) (Standard Curve Range: 12-29) |
|---|---|---|---|---|
| 1.5M NaCl | 2265 | 13 | 30 | 13 |
| 2.0M NaCl | 2939 | 13 | 64 | 14 |

TABLE 12-continued

Heparin Activity at Different NaCl Concentrations

| Sample Eluent | Heparin Activity (U/mL) Unpurified | Ct (Old) (Standard Curve Range: 11-28) | Heparin Activity (U/mL) Purified | Ct (New) (Standard Curve Range: 12-29) |
|---|---|---|---|---|
| 2.5M NaCl | 3007 | >31 | 1669 | 35 |
| 3.0M NaCl | 3068 | 35 | 2337 | 35 |

In the real time PCR assay described above, each purified sample was diluted to 2 ng/mL based upon its DNA concentration, and then 5 μL of each sample was used for assay. The total heparin amount in each reaction was calculated accordingly and are presented in Table 13. The results indicate a correlation between higher heparin activity and PCR inhibition.

TABLE 13

Correlations

| Purified Sample | Heparin Activity (mU/μL) | [DNA] (ng/μL) | Dilution Factor | Total Heparin per Reaction (mU) | Ct (New) (Standard Curve Range: 12-29) |
|---|---|---|---|---|---|
| 1.5M NaCl | 30 | 429.0 | 214.5 | 0.7 | 13 |
| 2.0M NaCl | 64 | 436.6 | 218.3 | 1.5 | 14 |
| 2.5M NaCl | 1669 | 498.7 | 249.4 | 33.5 | 35 |
| 3.0M NaCl | 2337 | 497.0 | 248.5 | 47.0 | 35 |

Example 7

This example describes a heparin spiking study used to determine the concentration of heparin that, when added to a PCR reaction, will influence the standard curve.

In order to determine the upper limit of heparin content tolerated by the real-time PCR reaction in the inventive method, a screening study was performed, in which a wide range of heparin dilutions were spiked with 0.1 ng of porcine genomic DNA. Real-time PCR was then performed and the Ct values for the spiked samples were compared with those obtained for non-spiked samples. Based on the results from the screening study, a narrower range of heparin concentrations was chosen for further testing. Porcine genomic DNA standard curves were spiked accordingly, and Ct values were obtained by real-time PCR. Table 14 shows the Ct value for test samples with 0.1 ng of porcine genomic DNA.

TABLE 14

Heparin Concentration v. Ct

| Amount of Heparin per Reaction (mU) | Ct Value (0.1 ng Porcine genomic DNA) |
|---|---|
| 0 | 14 |
| 0.2 | 15 |
| 0.4 | 15 |
| 0.8 | 15 |
| 1.6 | 16 |
| 3.2 | 18 |

TABLE 14-continued

Heparin Concentration v. Ct

| Amount of Heparin per Reaction (mU) | Ct Value (0.1 ng Porcine genomic DNA) |
|---|---|
| 4.8 | 19 |
| 6.4 | 21 |
| 9.6 | 26 |
| 12.8 | 31 |
| 19.2 | 35 |
| 25.6 | 35 |

Table 15 shows the standard curve ranges obtained with samples spiked with various amounts of heparin.

TABLE 15

Range of Ct Values

| Amount of Heparin per Reaction (mU) | Standard Curve Range |
|---|---|
| 0 | 11-30 |
| 0.4 | 12-30 |
| 0.8 | 13-30 |
| 1.6 | 13-31 |
| 0 | 9-27 |
| 3.2 | 13-29 |
| 6.4 | 17-33 |
| 12.8 | 27-N/A |

Based upon the results, Ct values fail to meet acceptance criteria when the amount of heparin is 6.4 mU or higher.

Example 8

This example describes an additional heparin spiking study which determined the highest acceptable level of heparin when heparinase is used for digestion. In this study, a series of heparin dilutions with and without an equal amount of heparinase were spiked into 0.1 ng of porcine genomic DNA and the Ct values were compared with non-spiked sample after real-time PCR was conducted according to the methods described above.

An initial screening study was performed with a wide range of heparin concentrations. The results of the screening study are presented in Table 16.

TABLE 16

Ct Dependence on Heparin Concentration

| Heparin (mU) | Ct | + Heparinase (mU) | Ct |
|---|---|---|---|
| 1000 | NA | 1000 | 20 |
| 500 | NA | 500 | 18 |
| 250 | NA | 250 | 17 |
| 100 | NA | 100 | 17 |
| 50 | NA | 50 | 16 |
| 25 | 29 | 25 | 17 |

Following the screening study, a narrower range of heparin amounts were selected for further testing to determine the level of heparin/heparinase digestion mixture that can be tolerated in Porcine genomic DNA standard curves. Porcine genomic DNA standard curves, prepared as described above, were spiked accordingly. Ct values were obtained by real time PCR and are presented in Table 17.

TABLE 17

Results of Spiking

|  | 1 ng | 0.1 | 0.01 | 1 pg | 0.1 pg | 0.01 pg |
|---|---|---|---|---|---|---|
| Control | 10/11 | 14 | 18 | 21 | 25 | 28 |
| 1000 mU | 15/14 | 20 | 22/23 | 23/24 | 23/24 | 23/24 |
| 500 mU | 13 | 18 | 21 | 22/23 | 23 | 23 |
| 250 mU | 12 | 17 | 20 | 22/23 | 23 | 23 |
| Control | 11 | 14 | 18 | 21 | 25 | 28 |
| 100 mU | 12 | 15 | 19 | 22 | 24 | 24 |
| 50 mU | 12 | 15 | 19 | 22 | 24 | 25 |
| 25 mU | 12 | 15 | 19 | 22 | 25 | 26 |

The non-spiking standard curve Ct values range from 10/11 to 28. The amplification for higher genomic DNA dilutions (1pg per reaction level and above) in spiked standard curves all have a Ct value of 22-24.

Melt curve analysis was performed to assess the consistency of DNA amplification. Results indicated that for all the spiked standard curves the amplified DNA was lower in molecular weight compared to the non-spiked standard curve. The non-spiked standard curve contained higher molecular weight product at high concentrations (lower dilutions) and lower molecular weight product at lower concentrations (higher dilutions).

The PCR products from both spiked (1000 mU) and non-spiked standard curve reactions were sequenced according to methods known in the art. The results indicate that all of the products are porcine in origin but show different amplification targets predominate depending on whether the heparin/heparinase mixture is present.

Various amounts (1000 mU, 500 mU, and 250 mU) of Heparin/Heparinase digestion mixture were similarly used to spike ruminant genomic DNA standard curves to determine if the same shift of amplification target occurred. The result indicated an inhibition of amplification in the presence of high levels of heparin/heparinase digestion mixture for the whole standard curve. The results of this experiment are summarized in Table 18, below.

TABLE 18

Spiking Results

|  | 1.0 ng | 0.1 ng | 0.01 ng | 1 pg | 0.1 pg | 0.01 pg |
|---|---|---|---|---|---|---|
| Control | 13 | 16 | 20 | 23 | 26 | 30 |
| 1000 mU | 16 | 21 | 24 | 28 | 31 | 34 |
| 500 mU | 15 | 19 | 22 | 26 | 30 | 33 |
| 250 mU | 14 | 18 | 22 | 25 | 29 | 32 |

Finally, various amounts (1000 mU, 500 mU, 250 mU, 100 mU, 50 mU, and 25 mU) of Heparin/Heparinase digestion mixture were also used to spike a modified Porcine standard curve (1.0 ng, 0.01 ng, 0.1 pg, and 0.001 pg) to see if the heparin/heparinase mixture could theoretically result in a false positive species identification. A comparison of the modified standard curve range to the standard range is presented in Table 19, below.

TABLE 19

Modified Standard Curves

| Routine Std Curve Range | 1.0 ng | 0.1 ng | 0.01 ng | 1 pg | 0.1 pg | 0.01 pg | N/A |
|---|---|---|---|---|---|---|---|
| Modified Std Curve Range | 1.0 ng | N/A | 0.01 ng | N/A | 0.1 pg | N/A | 0.001 pg |

The Ct values obtained for the modified standard curve in the presence of heparin/heparinase are presented in Table 20.

TABLE 20

Ct versus Heparin Concentration

|  | 1 ng | 0.01 ng | 0.1 pg | 0.001 pg |
|---|---|---|---|---|
| Control | 12 | 19 | 26 | 32 |
| 1000 mU | 16 | 23 | 24 | 24 |
| 500 mU | 14 | 22 | 24 | 24 |
| 250 mU | 13 | 22 | 24 | 24 |
| 100 mU | 13 | 20 | 24 | 25 |
| 50 mU | 13 | 20 | 25 | 26 |
| 25 mU | 13 | 20 | 26 | 28 |

The results of this assay indicate that the presence of heparin/heparinase digestion mixture causes an early amplification of higher dilutions in the porcine genomic DNA standard curve. This could result in a false positive species identification. Based on these findings, heparin/heparinase digestion mixtures are surprisingly incompatible with the inventive method, and heparinase does not address the problem of heparin inhibiting PCR DNA amplification.

Example 9

This example describes methods of sample preparation that were unexpectedly and surprisingly not suitable for use in the inventive methods described herein.

As described above in EXAMPLE 2, the present invention involves washing resin bound heparin samples with 1M NaCl followed by column purification prior to performing real-time PCR on the samples. Additional purification protocols were performed for comparison.

When real-time PCR was performed on samples prepared by washing resin bound heparin with 1M NaCl but without column purification, no amplification was observed. Surprisingly, there was also no amplification with 1M NaCl wash samples that were column and gel purified using QIAGEN QIAquick Gel Extraction kit and used for PCR. Also surprising, no amplification was observed when 1M NaCl wash samples were purified by QIAGEN Tissue and Blood kit prior to PCR.

Purification methods using concentrated 3M NaCl wash samples were also tested. When heparin bound resin was washed with 3M NaCl and was concentrated 10×, no amplification took place when real time PCR was attempted. Similarly, amplification was inconsistent and insufficient for use in the inventive methods with 5× concentrated 3M NaCl wash samples. Without being bound by any particular theories, these results are likely due to heparin activity content being too high for PCR (see EXAMPLES 6 and 7). Surprisingly, no amplification was observed when 10× concentrated 3M NaCl wash samples were first purified by agarose gel electrophoresis and DNA extraction using the QIAGEN (Germantown, Md.) QIAquick Gel Extraction kit prior to PCR. Also surprising, amplification was insufficient when 5×, and 40× concentrated 3M NaCl wash samples were gel purified, column purified and treated with heparinase digestion before PCR.

This example shows that numerous purification methods known to those of skill in the art were surprisingly inferior to the purification techniques used in the present invention.

Example 10

This example describes methods for performing qPCR in accordance with the invention from crude mucosal extracts, which are applicable to the prevention of contamination in porcine heparin and the speciation of heparin.

The same PCR protocol disclosed herein was performed on homogenized bovine and porcine mucosal extracts.

Table 21 presents the results of the use of ruminant primers (SEQ ID NOS: 20 and 21) to amplify porcine mucosal homogenates (appropriately ruminant negative) and Table 22 presents the results of the use of porcine primers (SEQ ID NOS: 3 and 4) using porcine mucosal homogenates (appropriately porcine positive).

TABLE 21

Porcine mucosal homogenates amplified with ruminant primers.

| Sample Type | | Ct Value Rep #1 | Ct Value Rep #2 | Ct Value Rep #3 | Average Ct Value (Standard Curve Range: 11-29) |
|---|---|---|---|---|---|
| Mucosa | Neat | 35.00 | 35.00 | 36.84 | 36 |
| Sample | 1:2 | 35.00 | 38.20 | 37.95 | 37 |
| Dilutions | 1:20 | 35.00 | 29.68 | 35.00 | 33 |
| | 1:50 | 38.30 | 35.00 | 28.65 | 34 |
| | 1:100 | 35.12 | 32.63 | 37.49 | 35 |

TABLE 22

Porcine mucosal homogenates amplified with porcine primers.

| Sample Type | | Ct Value Rep #1 | Ct Value Rep #2 | Ct Value Rep #3 | Average Ct Value (Standard Curve Range: 11-29) |
|---|---|---|---|---|---|
| Mucosa | Neat | 11.90 | 11.82 | 11.68 | 12 |
| Sample | 1:2 | 11.63 | 11.82 | 11.63 | 12 |
| Dilutions | 1:20 | 10.49 | 10.44 | 10.69 | 11 |
| | 1:50 | 10.83 | 10.92 | 10.72 | 11 |
| | 1:100 | 10.85 | 10.99 | 10.79 | 11 |

This replicate analysis indicates that mucosa can also be a suitable DNA source for use in accordance with the invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for identifying a biological contaminant in a crude heparin sample, wherein the biological contaminant is comprised of contaminant DNA of a unique sequence, the method comprising:
  (a) isolating DNA from the crude heparin sample, said isolating comprising:
    (i) simultaneously binding any DNA present and the heparin in the crude heparin sample to an anion exchange resin,
    (ii) differentially eluting any DNA present from the anion exchange resin with an elution solution, such that the heparin remains substantially bound to the anion exchange column, wherein the resin elution solution is from about 1.0 M to about 2.0 M sodium chloride,
    (iii), concentrating the eluted DNA, and
    (iv) using a silica based resin to limit the isolated DNA to fragments of at least 50 base pairs in length;
  (b) adding an aliquot of the isolated DNA from (a)(iv) to a PCR reaction mixture comprising a reporting molecule and a primer pair, wherein the primer pair is capable of selectively amplifying the contaminant DNA;
  (c) performing quantitative polymerase chain reactions on one or more aliquots of the concentrated isolated DNA extracted in step (a) using the PCR reaction mixture provided in step (b) to determine a threshold cycle (Ct) value of the sample of crude heparin;
  (d) calculating an average Ct value for the contaminant DNA in the crude heparin sample, wherein the average Ct value is an arithmetic mean of the Ct values determined in step (c); and
  (e) comparing the average Ct determined in step (d) with a standard curve of contaminant DNA concentration plotted against the Ct generated either in parallel or before, and
  (f) if the average Ct value of the sample is less than or equal to the average Ct value for a threshold level of contaminant DNA based on the a standard curve from step
  (e) the sample is positive for the contaminant and the crude heparin sample will not be used in the manufacture of a heparin product.

2. The method of claim 1, wherein the threshold Ct is determined in parallel with the heparin sample Ct.

3. The method of claim 1, wherein the threshold Ct is based on a limit Ct determined by prior experimentation.

4. The method of claim 1, wherein the isolating step (a) further comprising a filtration step after step (a)(ii) and before step (a)(iii), wherein said filtration step uses a 0.45 μm pore size filter.

5. The method of claim 1, wherein the anion exchange resin is an Amberlite resin.

6. The method of claim 1, wherein the elution solution comprises 1.0 M sodium chloride.

7. The method of claim 1, wherein the isolated DNA has a heparin concentration of less than 70 U/mL.

8. The method of claim 1, wherein a DNA compactor is added to the crude heparin prior to binding to the anion exchange column.

9. The method of claim 1, wherein the DNA compactor is hexamine cobalt.

10. The method of claim 1, wherein a PCR enhancer is added to the isolated DNA prior to qPCR.

11. The method of claim 1, wherein the PCR enhancer is selected from the group consisting of BSA, betaine, T4 phage gp32, and proteinase inhibitors.

12. The method of claim 1, wherein the contaminant is virus and virus-specific primers are used.

13. The method of claim 1, wherein the contaminant is material of ruminant origin.

14. The method of claim 13, wherein the PCR primers comprise SEQ ID NOS: 20 and 21.

15. The method of claim 1, wherein the contaminant is material of bovine origin.

16. The method of claim 1, wherein the PCR primers comprise SEQ ID NOS: 1 and 2.

17. The method of claim 1, wherein the reporting molecule is an intercalating dye.

18. The method of claim 17, wherein the reporting molecule is SYBR Green.

19. The method of claim 18, wherein the DNA is isolated from mucosa.

20. The method of claim 18, wherein the DNA is bound to an anion exchange resin simultaneously with heparin.

21. The method of claim 18, wherein the threshold Ct is determined in parallel with the heparin sample Ct.

22. The method of claim 18, wherein the threshold Ct is based on a limit Ct determined by prior experimentation.

23. The method of claim 18, wherein the isolating step (a) further comprising a filtration step after step (a)(ii) and before step (a)(iii), wherein said filtration step uses a 0.45 μm pore size filter.

24. The method of claim 18, wherein the anion exchange resin is an Amberlite resin.

25. The method of claim 18, wherein the elution solution comprises 1.0 M sodium chloride.

26. The method of claim 18, wherein the isolated DNA has a heparin concentration of less than 70 U/mL.

27. The method of claim 18, wherein a DNA compactor is added to the crude heparin prior to binding to the anion exchange column.

28. The method of claim 18, wherein the DNA compactor is hexamine cobalt.

29. The method of claim 18, wherein a PCR enhancer is added to the isolated DNA prior to qPCR.

30. The method of claim 18, wherein the PCR enhancer is selected from the group consisting of BSA, betaine, T4 phage gp32, and proteinase inhibitors.

31. The method of claim 18, wherein the contaminant is virus and the primers are specifically to that virus's DNA.

32. The method of claim 18, wherein the contaminant is material of ruminant origin.

33. The method of claim 31, wherein the PCR primers comprise SEQ ID NOS: 20 and 21.

34. The method of claim 18, wherein the contaminant is material of bovine origin.

35. The method of claim 33, wherein the PCR primers comprise SEQ ID NOS: 1 and 2.

36. The method of claim 18, wherein the primer pair is capable of selectively binding porcine DNA comprises SEQ ID NOS: 3 and 4 and the primer pair is capable of selectively binding contaminating DNA comprises one or both of SEQ ID NOS: 1 and 2, and SEQ ID NOS: 20 and 21.

* * * * *